United States Patent
Roth et al.

(10) Patent No.: US 6,663,616 B1
(45) Date of Patent: Dec. 16, 2003

(54) SET OF SURGICAL INSTRUMENTS

(75) Inventors: Klaus Roth, Ofterdingen (DE);
Hans-Jörg Saile, Hirrlingen (DE);
Mare Oliver Schurr, Tübingen (DE);
Gerhard Buess, Tübingen (DE);
Olivera Josimovic-Alasevic, Berlin
(DE); Karl-Gerd Fritsch, Berlin (DE)

(73) Assignee: co.don Aktiengesellschaft, Tetlow (DE)

( * ) Notice: Subject to any disclaimer, the term of this patent is extended or adjusted under 35 U.S.C. 154(b) by 0 days.

(21) Appl. No.: 09/380,012

(22) PCT Filed: Feb. 20, 1998

(86) PCT No.: PCT/EP98/00969
§ 371 (c)(1),
(2), (4) Date: Oct. 26, 1999

(87) PCT Pub. No.: WO98/36706
PCT Pub. Date: Aug. 27, 1998

(30) Foreign Application Priority Data

Feb. 24, 1997 (DE) .......................... 197 08 703

(51) Int. Cl.[7] .............................. A61B 1/00; A61B 17/00
(52) U.S. Cl. ............................. 606/1; 606/87; 600/114; 600/227
(58) Field of Search ................. 606/86, 87, 88, 606/130, 1; 600/102, 114, 227

(56) References Cited

U.S. PATENT DOCUMENTS

| | | | |
|---|---|---|---|
| 4,846,835 A | | 7/1989 | Grande .................. 623/11 |
| 5,397,323 A | | 3/1995 | Taylor .................. 606/130 |
| 5,511,564 A | | 4/1996 | Wilk .................... 128/898 |
| 5,540,675 A | * | 7/1996 | Hasson ................... 606/1 |
| 5,571,072 A | * | 11/1996 | Kronner ................. 600/102 |
| 5,810,712 A | * | 9/1998 | Dunn ..................... 600/114 |
| 5,824,007 A | * | 10/1998 | Faraz et al. ............ 606/130 |
| 5,876,332 A | * | 3/1999 | Looney ................... 600/102 |
| 5,931,832 A | * | 8/1999 | Jensen ..................... 606/1 |
| 5,954,635 A | * | 9/1999 | Foley et al. ............. 600/114 |
| 6,361,488 B1 | * | 3/2002 | Davison et al. ........... 600/102 |

FOREIGN PATENT DOCUMENTS

| | | |
|---|---|---|
| DE | 4307876 | 7/1994 |
| DE | 4340707 | 1/1995 |
| DE | 19609034 | 9/1996 |

OTHER PUBLICATIONS

M. Brittberg et al.; Rabbit Articular Cartilage Defects Treated with Autologous Cultured Chondrocytes; Clinical Orthopaedics and Related Research, No. 326, 1996; pp. 270–283.

E. Markgraf et al.; Der Unfallchirurg; Springer Verlag, 60th Annual Meeting of the Deutsche Gesellschaft für Unfallchirurgie e. V., Nov. 20–23, 1996 Berlin, Abstracts; 283.

* cited by examiner

*Primary Examiner*—Linda C. M. Dvorak
*Assistant Examiner*—Jocelyn Ram
(74) *Attorney, Agent, or Firm*—Norris McLaughlin & Marcus

(57) ABSTRACT

The invention relates to a surgical set of instruments used to treat surfaces of cartilage, bone or body tissue, which set comprises a surgical instrument 1 and a guide device 2 to guide said instrument and/or a tissue applicator 3 for inserting tissue on a defect to be covered. In the meaning of the present invention, the surgical instrument, which can be moved in a circular, elliptical or another way with the aid of the guide device 2 according to the invention, is understood to be a shaver, a scalpel, a drill, a curette, a syringe, or a probe. Depending on the surgical problem, however, other instruments for cutting, milling, punching, sewing, or setting bores in cartilage, bone or body tissue, or injecting operating aids such as glues may also be moved in a specific surface profile using the guide device of the invention.

16 Claims, 8 Drawing Sheets

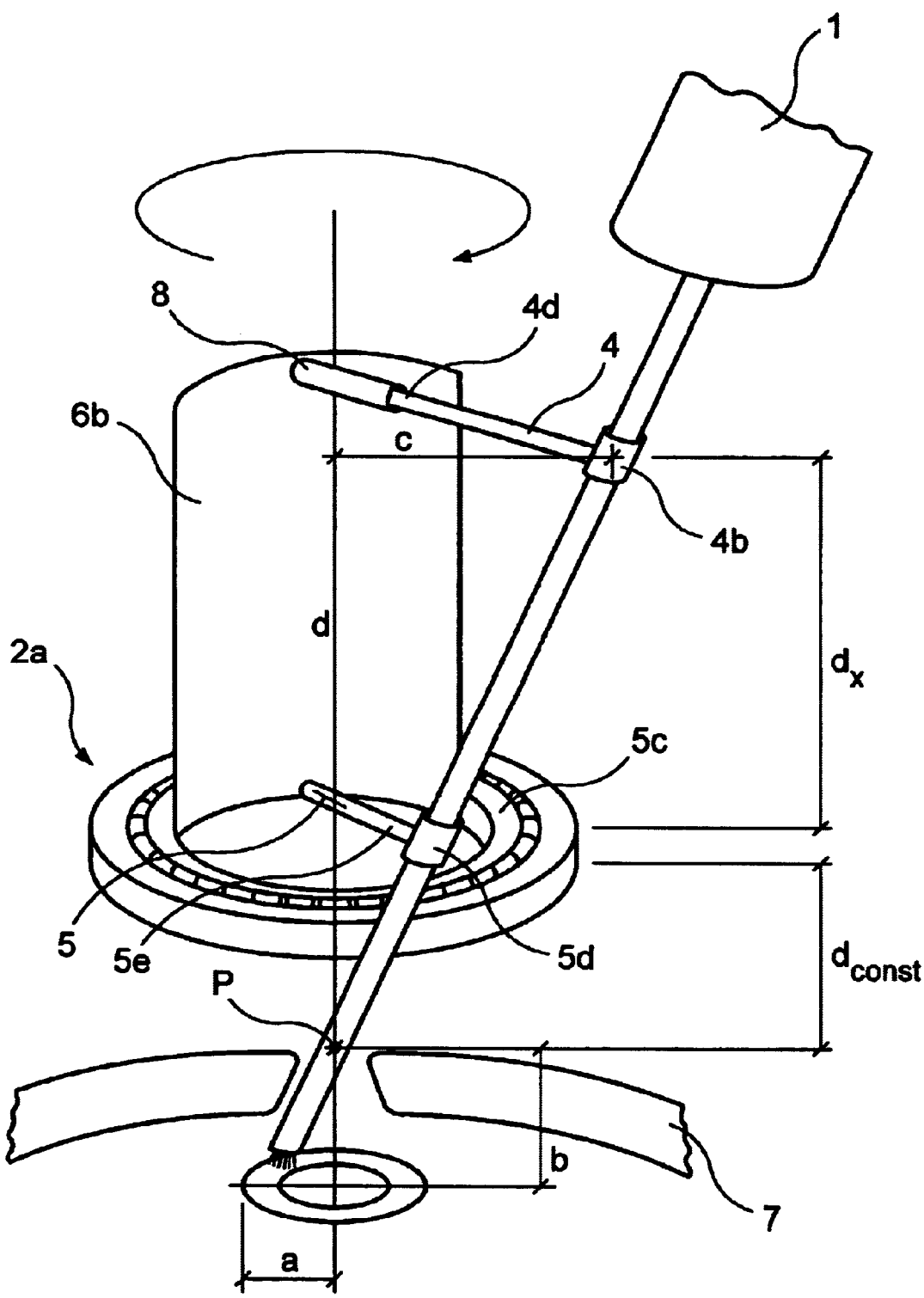
F I G. 2

SET OF SURGICAL INSTRUMENTS

BACKGROUND OF THE INVENTION

1. Field of the Invention

The invention relates to a surgical set of instruments used to treat surfaces of cartilage, bone or body tissue, which set comprises a surgical instrument 1 and a guide device 2 to guide said instrument and/or a tissue applicator 3 for inserting tissue on a defect to be covered. In the meaning of the present invention, the surgical instrument, which can be moved in a circular, elliptical or another way with the aid of the guide device 2 according to the invention, is understood to be a shaver, a scalpel, a drill, a curette, a syringe, or a probe. Depending on the surgical problem, however, other instruments for cutting, milling, punching, sewing, or setting bores in cartilage, bone or body tissue, or injecting operating aids such as glues may also be moved in a specific surface profile using the guide device of the invention.

The surgical set of instruments according to the invention is particularly advantageous for microinvasive work on most various organs, e.g. the intervertebral disk, and especially in arthroscopic work. For example, cartilage defects represent a major problem in reconstructive joint surgery as a result of the lacking regenerative capability of cartilage, giving rise to joint mechanical disorders, increasing cartilage wear in adjacent areas, and post-traumatic arthroses. "Der Unfallchirurg", published by E. Markgraf and K. E. Rehm, Springer Verlag, 60th Annual Meeting of the Deutsche Gesellschaft fur Unfallchirurgie e.V., Nov. 20–23, 1996, Berlin, Abstracts, Forum: Experimentelle Unfallchirurgie, page 283, describes a method of biotechnological cartilage reconstruction using cultivated chondrocytes and a collagen sponge. Using this method, the in vitro production of autologous cartilage tissue in any desired shape and size is possible by isolating cartilage cells from the kneecaps of freshly slaughtered calves and placing them on a collagen sponge. Thereafter, the chondrocyte-collagen fleece artificial structure is cultivated with addition of L-ascorbic acid, L-glutamine, antibiotics, and fetal calf serum.

Subsequently, this artificial structure is implanted subcutaneously in naked mice, and new cartilage is generated in the form of the collagen sponge used. Hyaline cartilage is detected, as well as type II collagen which is specific for this cartilage.

A similar method is described in the U.S. patent specification U.S. Pat. No. 4,846,835. This written specification discloses the application of a patch of periosteum on the cartilage defect following implantation of the chondrocyte-collagen material to effect mechanical fixation thereof. Said U.S. Pat. No. 4,846,835 describes the transplantation procedure on rabbits. There is no description of a device for collecting and applying periosteum tissue that would ensure efficient operation with high quality and at the same time, minimize the risk for a patient. Operations are performed on open knees, the periosteum patch is collected with a scalpel and likewise, the lesion is prepared using a scalpel.

2. Description of the Related Art

Likewise, in "Clinical Orthopaedics and Related Research" No. 326, pp. 270–283, 1996, Matts Brittberg et al. describe this transplantation method using autologous chondrocytes on New Zealand rabbits where, inter alia, autologous chondrocytes are cultivated on a carbon fiber fleece, and this chondrocyte/carbon fiber fleece structure is implanted.

However, this reference, as well as numerous other publications by Mats Brittberg et al. solely describe transplantation procedures on open knees. Meanwhile, this open knee transplantation method is also performed in human medicine clinical practice.

However, classical operations on open joints always involve the risk of wound inflammation, the postoperative pain is considerable, the period of rest in hospitals is longer, as is the rehabilitation period.

SUMMARY OF THE INVENTION

It is the object of the present invention to develop a surgical set of instruments permitting accurate guidance of the surgical instrument according to the area to be treated, which allows operating both on open defects and in a microinvasive fashion and, in particular, is suitable for arthroscopic operation.

More specifically, it is the object of the invention to develop an efficient transplantation method for the biotechnological cartilage reconstruction on humans, which utilizes the in vitro cultivation of autologous cartilage cells, their transplantation into the cartilage defect, and the closure of said defect using periosteum tissue, but does not require open joint operations.

The object of the invention is accomplished by means of a surgical set of instruments comprising a surgical instrument (1) and a guide device (2) for orthogonal or horizontal treatment of cartilage, bone or body tissue surfaces according to the claims. The guide device comprises one proximal and one distal guide element allowing a reproducible motion of the surgical instrument (1) through an invariant point P, where the size of the area to be treated (preferably a circle or an ellipse) can be varied by varying the distance between the two guiding elements. The size of the tissue area to be treated is determined by the ratio of the distance between the two guide elements and the distance from the invariant point to the area of tissue to be treated, with simultaneous consideration of the angle between the imaginary straight lines a and b, where straight line a passes through the invariant point and centrally through the geometrical figure formed by the guide elements, while straight line b passes through the invariant point and tangentially to the most distant point through the geometrical figure formed by the guide elements.

BRIEF DESCRIPTION OF THE DRAWINGS

FIG. 2 illustrates another embodiment of guide device 2 for vertical set-up on the area to be treated;

DESCRIPTION OF THE PREFERRED EMBODIMENT

Preferred embodiments of the guide device (2) are illustrated in the FIGS. 1 through 8. According to the invention, the surgical set of instruments consists of the surgical instrument 1 and a guide unit wherein the surgical instrument 1 is guided in such a way that areas of various sizes can be treated depending on the size of the defect. Optionally, the set of instruments comprises a tissue applicator 3 for applying tissue on a defect to be covered.

While the guide device according to claims 1–4 is developed to be placed vertically on, e.g. a cartilage, bone or body tissue surface to be cut, milled or provided with bores in a microinvasive fashion, the guide device according to claims 5–6 allows tangential operation. Relatively often, the problem arises in arthroscopy, for example, that operations cannot be performed vertically on the affected part of the knee but rather, the instruments have to be introduced laterally and operations have to be performed tangentially. In particular, this is the case with defects on the rear side of a kneecap.

According to the invention, the surgical instrument 1 may also be a syringe which is guided in guide device 2 so that auxiliary agents required for operation, such as fibrin glue, can be applied on site via a long cannula in a well-aimed fashion on the border of an area adjustable using guide device 2, which area possibly has been milled out previously and now requires gluing.

Figure 1:
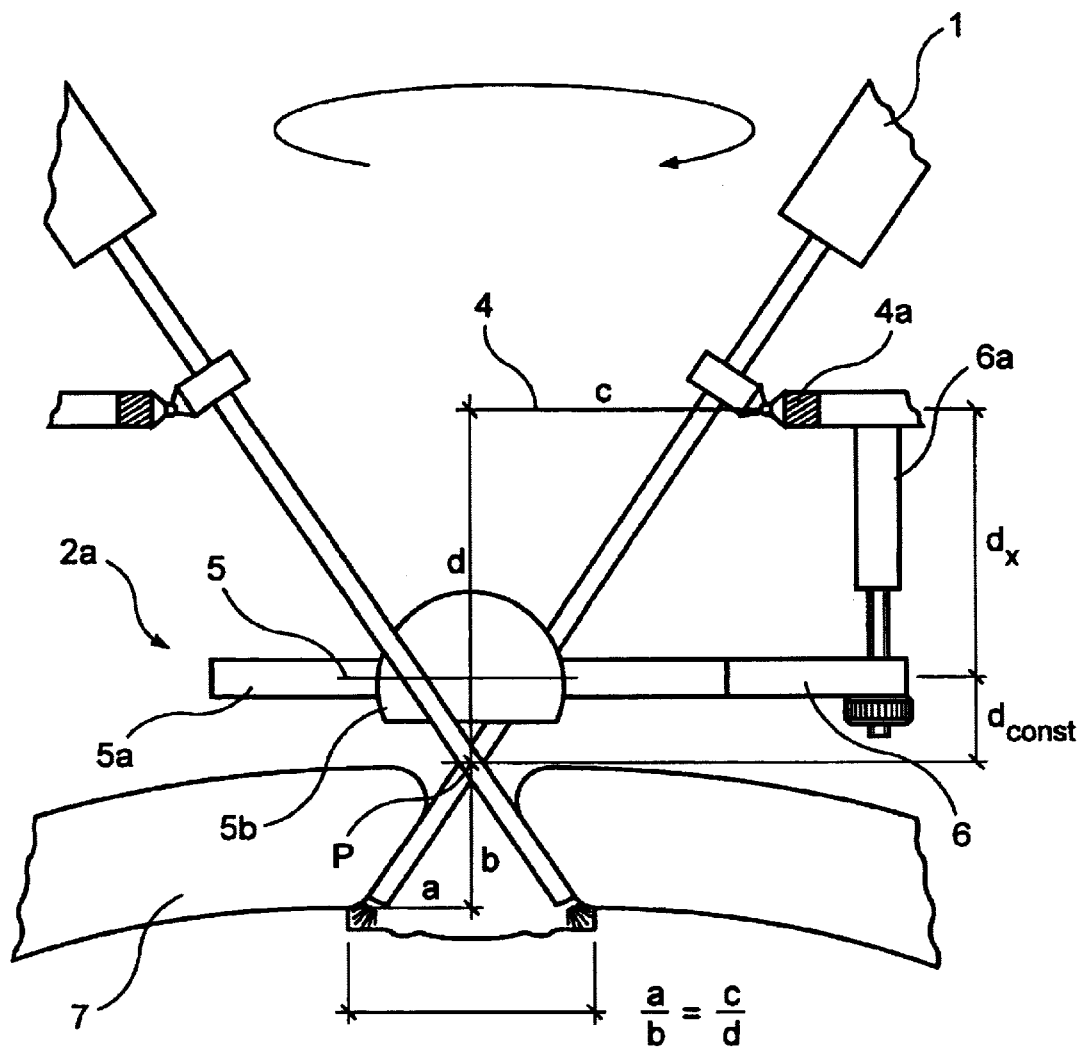
FIG. 1 shows a sectional view of an embodiment of guide device 2 for vertical set-up on the area to be treated.
Figure 3:
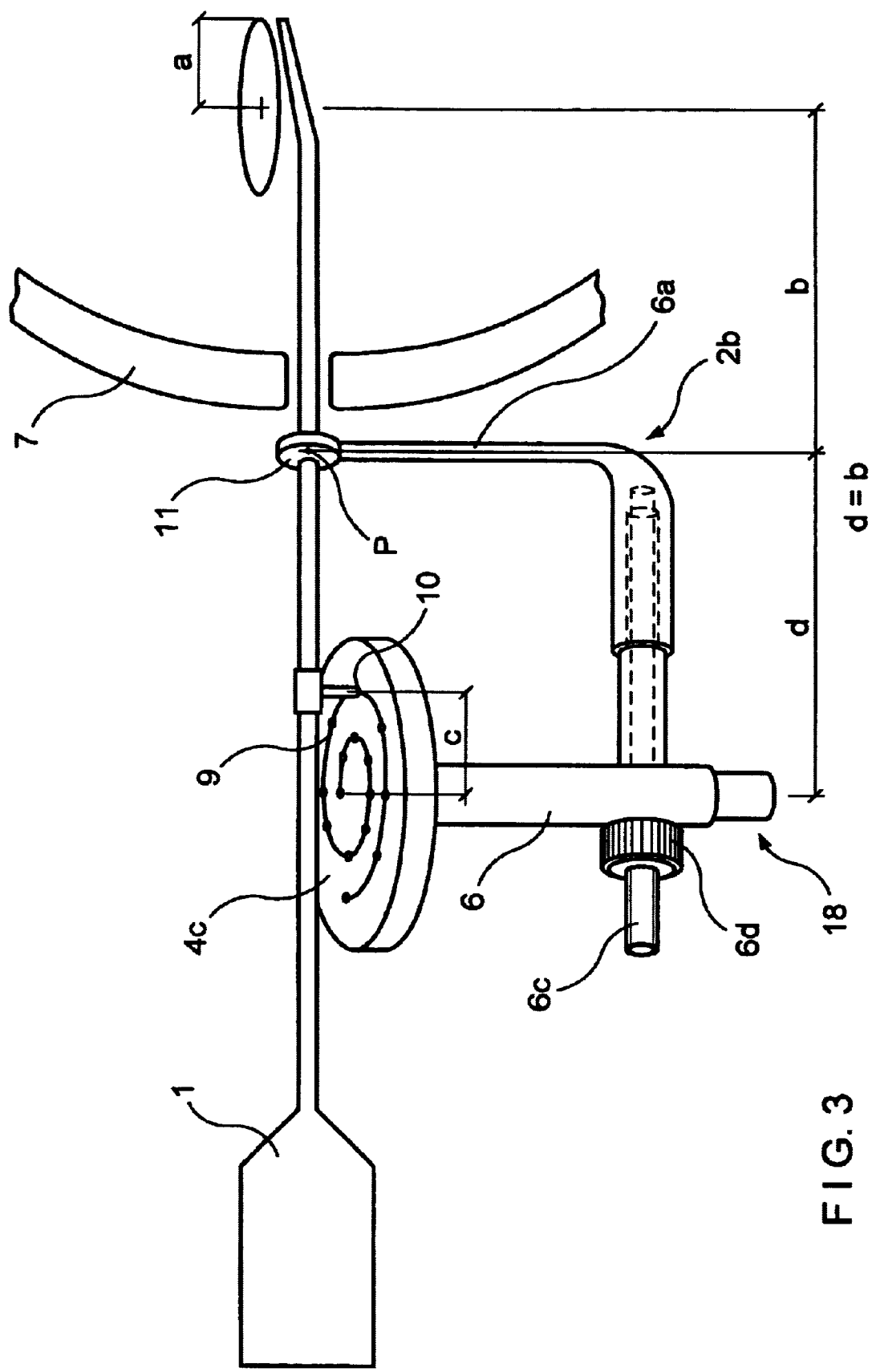
FIG. 3 illustrates an embodiment of guide device 2 for tangential set-up.
Figure 4:
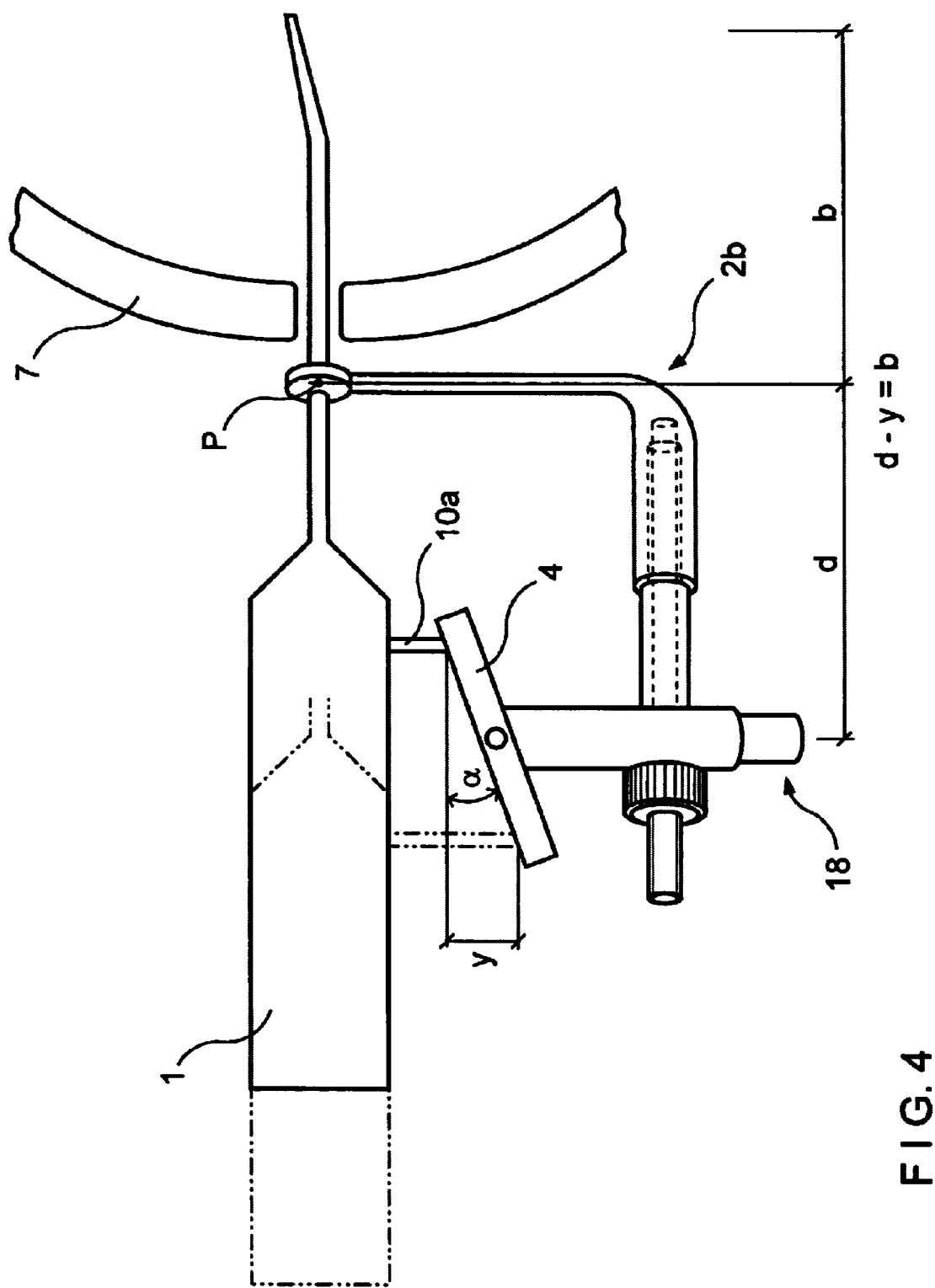
FIG. 4 illustrates another embodiment of guide device 2 for tangential set-up.
Figure 8:
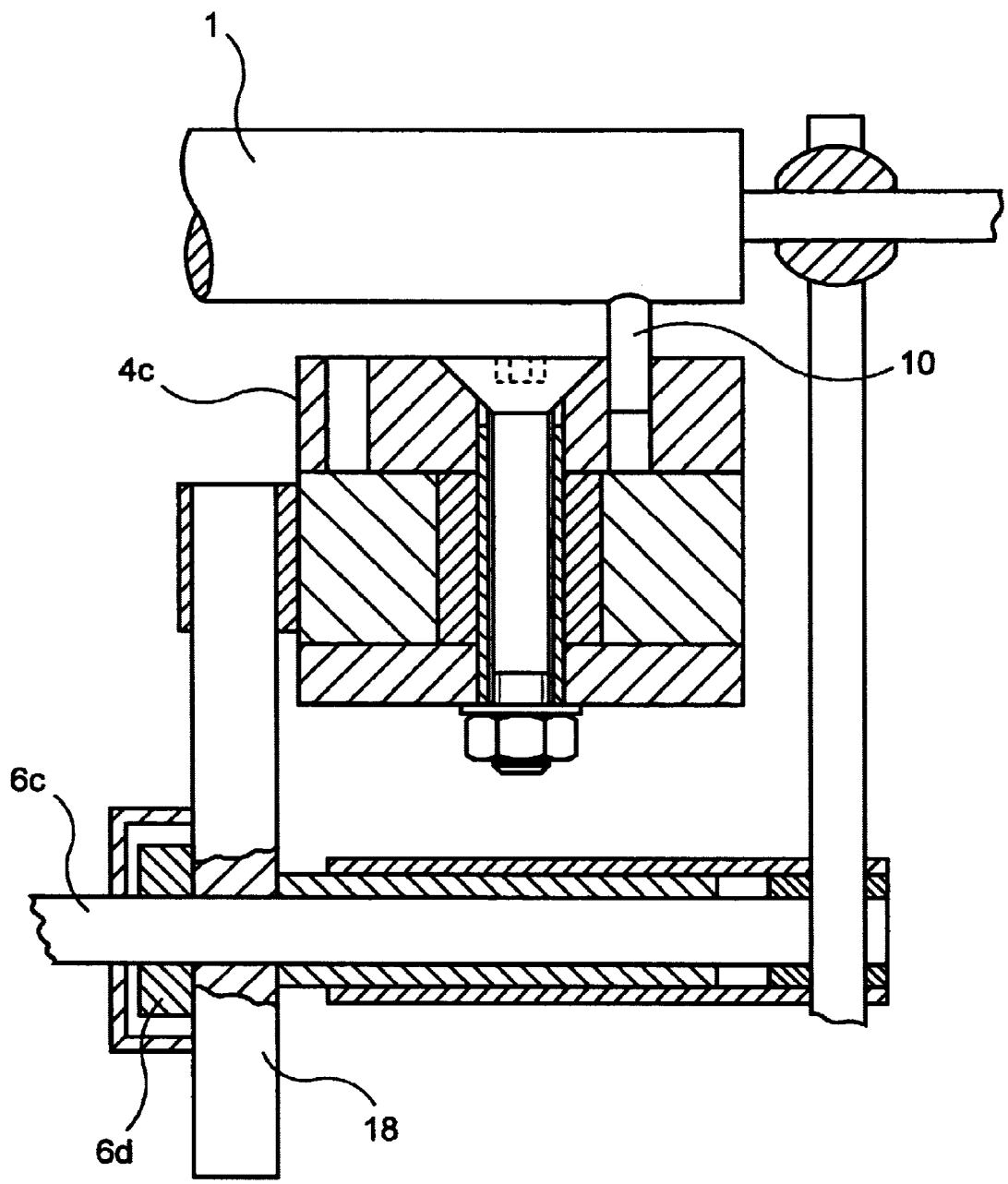
FIG. 8 shows a detailed sectional view of the guide device 2 in accordance with FIG. 3.

Preferred embodiments for orthogonal treatment of tissue surfaces are illustrated in FIGS. 1 and 2. FIGS. 3, 4 and 8 show preferred embodiments of a guide device used for horizontal treatment of cartilage, bone or body tissue surfaces.

A first preferred embodiment of the guide unit 2 for orthogonal treatment is illustrated in sectional view in FIG. 1 and described in claim 2.

The principle of guiding the surgical instrument 1 in this variant is based on the fact that two guide elements having different diameters 4a and 5a rest in concentric bearings at an adjustable distance d. The upper guide ring 4a which is larger in size serves to accommodate the surgical instrument 1. The radius c of this ring is constant. A horizontally rotatable ball 5b having an eccentric bore rests in bearings in the lower guide ring 5a. The surgical instrument 1 is passed through this bore. The slope angle of the surgical instrument 1 can be varied by varying the distance d of the two guide rings relatively to each other.

The bore in ball 5b of the lower guide ring 5a must be eccentric, so that the invariant point P will be situated below the lower guide ring 5a. The invariant point should be the penetration point through the skin and be in the center of the skin layer. In this way, it is possible to guide the surgical instrument along the upper guide ring 4a and maintain the penetration point through the skin in the same position each time. Owing to the different size of the upper and lower guide rings 4a, 5a, the distance d between the two rings has an effect on the size of the area to be treated according to the equation a:b=c:d, so that the radius of the area to be treated can be adjusted by varying the distance d of the two guide rings relative to each other. The line b corresponds to the distance between the invariant point P and the center of the area to be treated. Said distance between the lower guide ring 5a and the invariant point P is constant.

A second preferred embodiment of the guide device 2 for orthogonal operation can be inferred from FIG. 2 and is described in claim 3.

In this embodiment, a half-shell 6b of a tube is rotatably arranged vertically to the ring plane in an inner ring 5c of a bearing, preferably a ball bearing. Ideally, the inner diameter of said tube is slightly larger than the outer circumference of the surgical instrument 1. At the accommodation site of the half-shell in the bearing, there is a lower accommodation sleeve 5d for the surgical instrument 1, which sleeve is shiftable within the diameter of the bearing. The accommodation sleeve 5d represents the lower guide plane. The distance of the accommodation sleeve 5d from the center of the diameter through the ball bearing has an effect on the position of the invariant point P below the bearing. At the top of half-shell 6b, there is a pivotable securing element 8 for the surgical instrument 1. The upper accommodation sleeve 4b is fixed to said securing element via a joint element 4d, so that a circular upper guide plane 4 is generated when the half-shell is rotated. In order to enlarge the circular area of radius a in the patient, the securing element 8 has to be pivoted. In this embodiment, the radius c represents the vertical distance from the center of the upper accommodation sleeve 4b to the center line of half-shell 6b.

A guide device to be set up tangentially on an area to be cut, milled, provided with bores, or sewn circumferentially is described in claim 5 and illustrated in FIGS. 3 and 8. Based on the first preferred embodiment of guide device 2 to be set up vertically, the upper guide plane 4 in the present case is rotated by 90°, so that the upper guide plane, which has the form of a disk 4c in the present case, is tightly joined to a holder 6, forming a plane with same. The surgical instrument 1 is inserted via a guide pin 10 into one of the bores 9 arranged helically on the disk, so that a rotary motion of the surgical instrument 1 is achieved by rotating the disk and thus, tangential treatment of a lesion of radius a is possible. In this variant, therefore, the surgical instrument 1 is guided indirectly. One precondition for compliance with the equation a:b=c:d and for the fact that the radius a of the area to be treated is determined by the respective radius c from the center of the disk to the bore into which the surgical instrument 1 has been inserted, is that the lines b and d are equal in length. If these lines are not equal in length, an elliptical rather than a circular area will be treated. In a particularly preferred embodiment, the distance d can be adjusted via a threaded rod 6c by means of knurled nut 6d (cf., FIGS. 3 and 8). As can easily be seen, it is advantageous in the present variant that the head of the surgical instrument 1 is bent. Using these slightly cranked instruments, it is possible to reach any point, including the rear side of a kneecap.

Another embodiment of the guide device 2 for tangential set-up is described in claim 6 and illustrated in FIG. 4. In this case as well, the surgical instrument 1 is inserted indirectly. Compared to the embodiment of FIG. 3, the only difference in this variant is a different design of the upper a guide element 4, so that the distances b and d are not required to have equal length in order to be capable of treating circular areas. In this case, the length of line b is determined by the difference of the d–y distances.

In all the embodiments of the guide device according to the invention it is possible to provide one of the guide elements 4 or 5 with a graduation so that, e.g. bores set in cartilage or bone by means of the surgical instrument 1 can be determined by using said graduation and possibly transferred to a patch of tissue to be applied on a defect to be covered. In this way, a proper predetermination of the position of bone pins possibly to be inserted can already be made in the tissue.

Obviously, other embodiments of the principle according to the invention are conceivable which can be carried out by a person skilled in the art without inventive activity. Thus, the guide devices of FIGS. 3 and 4 can be designed in such a way that when interrupting the regular motion of the surgical instrument 1 by moving back and forth, not only round shapes but also notches or protrusions in the shape can be determined and transferred (e.g., on tissue) using said graduation. In the embodiments of FIGS. 3 and 4, for example, this can be achieved by mounting the guide pin 10 on the shank of the surgical instrument 1 in a transversely shiftable fashion.

Using the surgical instrument 1 of the invention and the accessory guide device 2, not only transfers of the surface of a defect to the outside but also three-dimensional transfers can be accomplished by applying twp components crosslinking on site (e.g., a biopolymer and a crosslinker) to, e.g. a bone or cartilage defect using a double-lumenal syringe. In this way, the defect can be modeled.

Of course, the surgical instrument 1 of the invention, including its guide device 2, can also be controlled by electronic means or may be power-driven. Also, by using the guide device 2 and a probe as surgical instrument 1, defects can be scanned and transferred to the outside.

Figure 5:
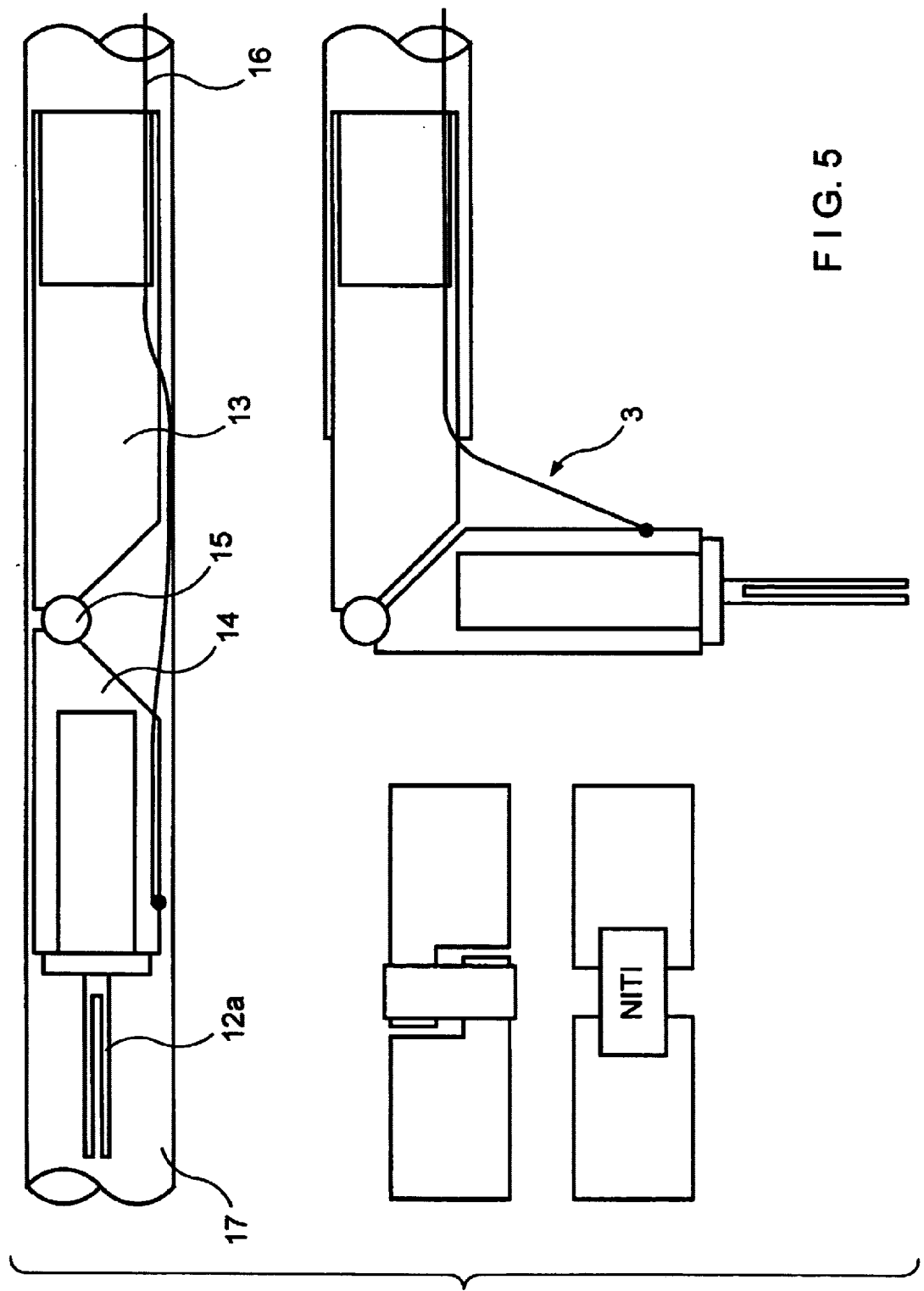
FIGS. 5, 6, 7 illustrate tissue applicator embodiments according to the invention.

Another possible component of the surgical set of instruments according to the invention is a tissue applicator 3 for applying tissue on a defect to be covered. Any tissue absorbable by the body, but also periosteum or other endogenous tissue is understood to be a tissue in the meaning of the invention. According to the invention, the tissue applicator 3 consists of a holder 12 for the tissue, which is arranged rotatably and/or pivotably in a bearing on a tube shaft 13. A preferred embodiment of such a tissue applicator 3 is illustrated in FIG. 5. The tissue applicator 3 as illustrated has a forked holder 12 which can be adjusted to the length of the tissue patch and is arranged rotatably in a bearing in an accommodation element 14 opposite the tube shaft 13, which element can optionally be angled. In the present case, a link joint 15 is provided for angling; however, a superelastic joint between the tube shaft 13 and the accommodation element 14 is also possible. In practical use, the tissue applicator is introduced into the body in a surrounding tube 17 via a so-called frocar sleeve. The angling of the accommodation element is controlled using a control wire 16.

Figure 6:
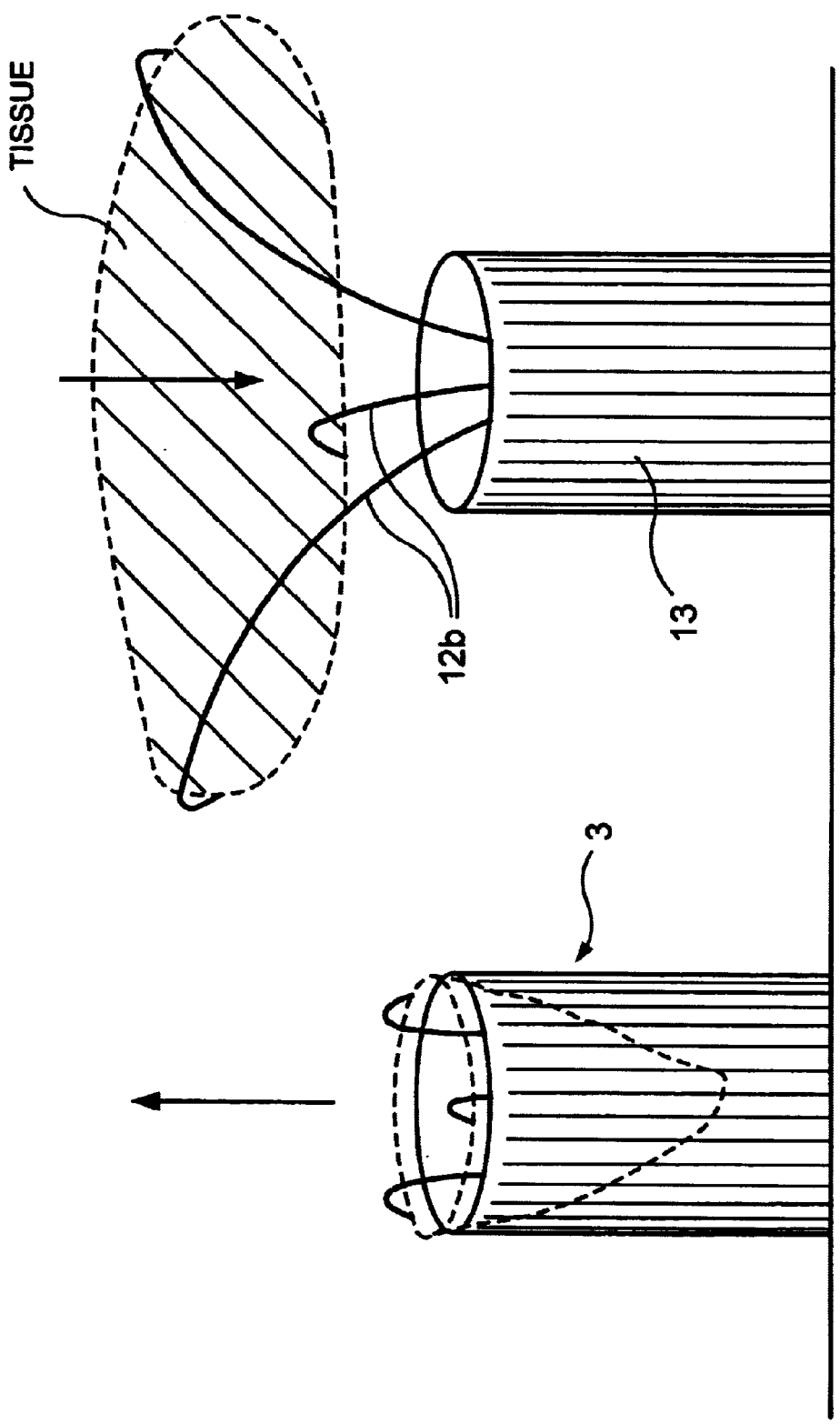

Another feasible embodiment of the tissue applicator 3 according to the invention is described in claim 11 and illustrated in FIG. 6. In this embodiment, the holder 12 consists of hooks arranged pivotably in the tube shaft 13. The hooks must be highly flexible and, of course, consist of a medically approved material such as a nickel-titanium alloy. The tissue patch is suspended in the hooks 12 and pulled into the tube shaft 13 or pushed therein using some auxiliary means. Now, when pushing out the hooks 12, they put up the tissue like an umbrella as a result of their elasticity.

Figure 7:
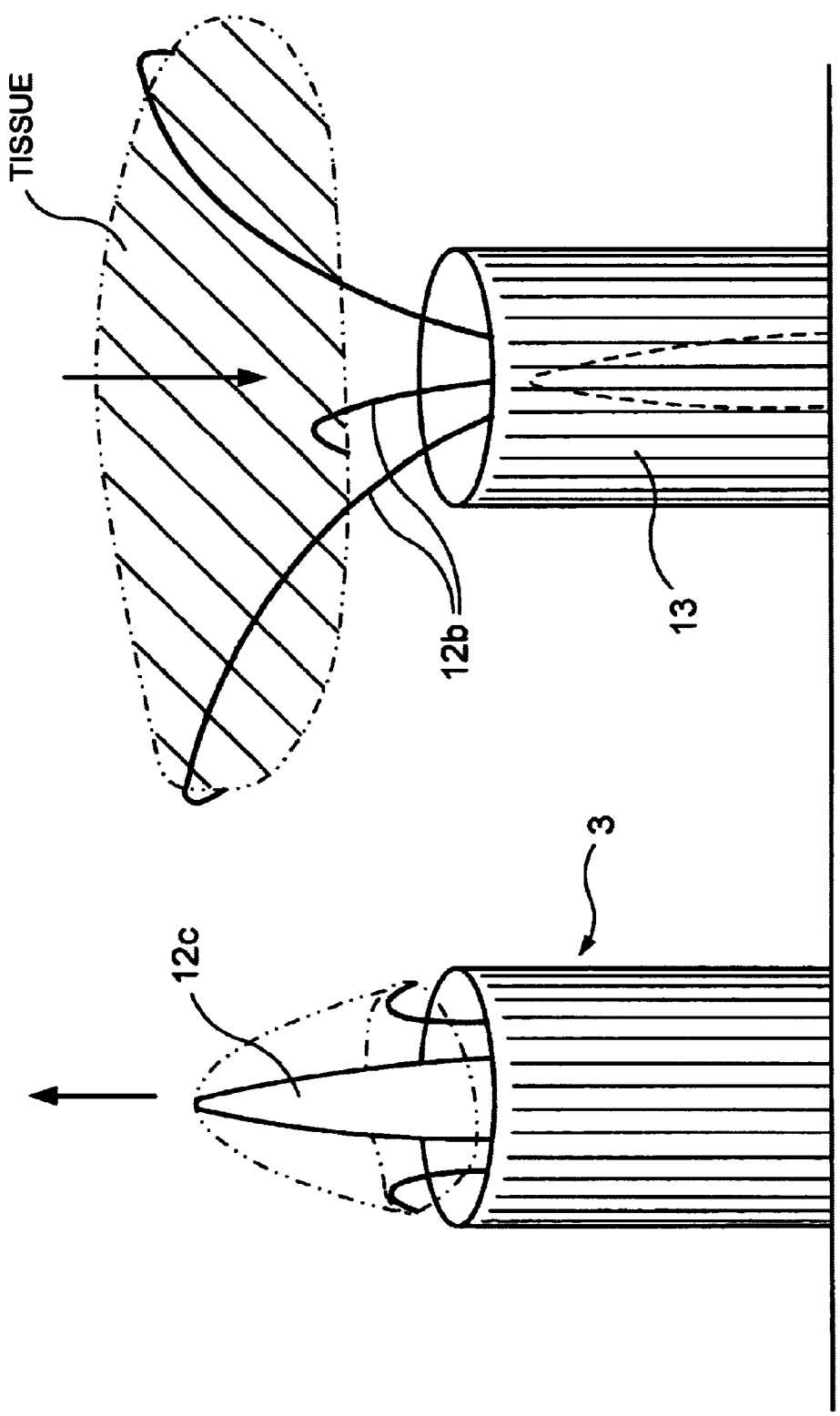

In another embodiment, the tissue applicator 3 according to the invention additionally has a pivotable mandrel 12 in accordance with FIG. 7, which can be made of a medically approved metal or plastic material. This variant ensures that the tissue, particularly periosteum, does not have to be Inserted in the tube shaft 13, which might be difficult as a result of the size disproportion. Owing to the variant of FIG. 7 according to the invention, the tissue is suspended in the hooks 12 and spread over the extended mandrel 12. When withdrawing the mandrel 12 with simultaneous extension of the hooks 12, the tissue is put up and can now be applied on a defect.

In principle, the tissue applicator 3 of the invention can be useful in any insertion of tissue into the body, e.g. in cartilage reconstruction in the knee for inserting periosteum, or when inserting a screen in repairing an inguinal hernia.

As will be apparent from the above statements, the guide device 2, together with a shaver, can be used as a surgical instrument 1, e.g. in the treatment of cartilage defects and in cutting out healthy cartilage to be cultivated in vitro, in affixing a groove around the cartilage defect, and in cutting periosteum tissue which is to cover the cartilage defect.

In addition to the surgical set of instruments, the invention therefore relates to a transplantation method of biotechnological cartilage reconstruction, which makes use of an in vitro cultivation of autologous cartilage cells and their transplantation into the scooped cartilage defect prepared with a ring groove, and the closure of the defect using periosteum tissue. The transplantation procedure is carried out using the inventive surgical set of instruments according to claims 1 through 11. Thus, the guide device 2 and its preferred embodiments in accordance with FIGS. 1 and 2 and a scalpel as surgical instrument 1 can be used in the circular removal of periosteum from the shin. Likewise, these devices are used to affix a ring groove around a defect in the region of the knee, provided it is accessible directly from the front. In addition, the guide device 2 and a syringe as surgical instrument 1 can be used to attach the periosteum patch to the ring groove. In case a defect in the region of the knee can only be accessed laterally, the guide device 2 in accordance with FIGS. 3 and 4 has to be used.

In a preferred embodiment, for repairing a cartilage defect accessible from the front, the transplantation method according to the invention using the set of instruments of the invention is performed as follows:

A cartilage defect in the knee is worked out to a depth required for operation. As the cartilage defect is accessible from the front, the guide device 2 according to FIG. 1 is mounted using well-known holding systems, and adjusted accordingly. The distance between the upper and lower guide rings 4a, 5a is predetermined by the size of the defect. In this way, the size of the circle described by the shaver in the knee can be determined. Ideally, the area to be treated should be selected so as to be somewhat larger than the largest diameter of the defect, so that a circular step around the defect can be milled with the shaver.

In a second operation step, the periosteum in the shin of the patient is cut using the guide device 2. The size of the periosteum patch is predetermined by this cut. Owing to the distance between the lower and upper guide ring already determined in operation step 1, the periosteum patch has the proper size and can subsequently be fitted properly into the scooped step during retransplantation into the knee. Now, the periosteum is removed from the bone by means of usual arthroscopic instruments and collected. It has to be stored under sterile conditions until transplantation.

In a third operation step, the periosteum is wound on, e.g., the tissue applicator of the invention according to FIG. 5 and introduced into the knee. If it appears necessary in the course of the examination to provide bores for the bone pins for easy insertion thereof into the cartilage mass, these bores in the knee should be made by means of a drill as surgical instrument 1 and with the aid of guide device 2. For this purpose, the upper guide ring 4a has a graduation scale permitting transfer of the bore holes from the knee to the periosteum patch. Hence, the periosteum patch is perforated with the aid of the guide device 2 of the invention including a drill or curette as surgical instrument 1. Owing to this procedure, the retrieval of the bore holes through the periosteum is substantially facilitated during application in the knee.

Now, the periosteum is secured in the cartilage of the knee through the perforation using a first bone pin. By laterally moving the tissue applicator 3, the periosteum patch then is unwound until a second pin is to be set. For further pins, the periosteum can be unwound further until the periosteum is secured with the required number of pins. The required number of pins is determined by the size of the defect to be treated.

In a fourth operation step, a double-lumenal syringe filled with fibrin glue is clamped in guide unit 2 in order to seal the periosteum patch against the healthy cartilage tissue. The fibrin then is injected directly through a double-lumen cannula. In this way, the periosteum patch can be sealed against the cartilage using an exceedingly small amount of fibrin, because the fibrin is placed exactly on the spot by adjusting the guide unit 2.

It appeared that such inventive "gluing" of the periosteum to the milled groove results in such durability that mounting of bone pins is entirely unnecessary in some cases.

In the fifth and last operation step, the in vitro cultivated autologous chondrocytes are injected under the periosteum, and the surgical wound is closed.

Reference List

1 Surgical instrument
2 Guide device for the surgical instrument
3 Tissue applicator
4 Upper guide element
4a Upper ring
4b Upper accommodation sleeve
4c Rotatable disk
4d Joint element
5 Lower guide element
5a Lower ring
5b Ball or hemisphere with eccentric bore area to be treated
5c Inner ring of a bearing
5d Lower accommodation sleeve
5e Joint element
6 Holder
6a Joint element
6b Half-shell
6c Threaded rod
6d Knurled nut
7 Skin
8 Longitudinally adjustable securing element
9 Bores
10 Guide pin on surgical instrument
10a Longitudinally adjustable guide pin
11 Guide sleeve
12 Holder for tissue
12a Forked holder
12b Holder consisting of hooks
12c Mandrel
13 Tube shaft of the tissue applicator
14 Accommodation element
15 Link joint
16 Control wire for angling
17 Surrounding tube
18 Table holder
a Radius of the area to be treated
b Distance between invariant point p and area to be treated
c Radius of upper guide plane
d Distance between upper and lower guide plane or between upper guide plane and lower guide sleeve (11)
y Radial compensation line (line sinus a of angle α)
p invariant point

What is claimed is:

1. A surgical set of instruments, comprising a surgical instrument and a guide device for orthogonal treatment of cartilage, bone or body tissue surfaces, wherein the guide device has a first guide element for circular guiding of the surgical instrument and a horizontally rotatable second guide element, and both first and second guide elements are connected via a holder, wherein the first guide element is arranged in such a way that a first radius c of a first guide plane generated in circular guiding of the surgical instrument is larger than a second radius of a second circular guide plane generated with the second guide element, and the surgical instrument passes eccentrically through the second guide plane in a way so as to pass through an invariant point (P) below the second guide element, and a radius a of an area to be treated with the surgical instrument can be adjusted by varying a distance d of the first and second guide elements relative to each other according to equation a:b=c:d, where b is the distance between the invariant point (P) and a center of the area to be treated.

2. The surgical set of instruments according to claim 1, wherein the first guide element in the guide device is a first ring, the guide element consists of a second lower ring and a ball or hemisphere which is arranged in a bearing therein and has an eccentric bore through which the surgical instrument is passed, the first and second rings are joined to each other by a joint element, and the second ring is arranged vertically adjustable on the joint element via the holder.

3. The surgical set of instruments according to claim 1, wherein the second guide element in guide device is a third inner ring of a bearing wherein a half-shell is rotatably arranged vertically to a ring plane of the third inner ring, at the bottom of which situated in the bearing, an accommodation sleeve for the surgical instrument is affixed via a joint element in such a way that the surgical instrument passes eccentrically through the third inner ring of the bearing, and at the top of which an accommodation sleeve for the surgical instrument is affixed to a longitudinally adjustable securing element via a joint element, so that the radius c of the first guide plane generated in circular guiding of the surgical instrument is equal to a vertical distance from a center of the accommodation sleeve to a center line of the half-shell.

4. The surgical set of instruments according to claim 1, wherein one of the first and second guide elements has a graduation.

5. The surgical set of instruments according to claim 1, wherein the set additionally comprises a tissue applicator for applying tissue on a defect to be covered, consisting of a holder for the tissue and a tube shaft, the holder being arranged optionally rotatably and/or pivotably in a bearing in the tube shaft.

6. The surgical set of instruments according to claim 5, wherein the tissue applicator has a forked holder which is rotatably arranged in a bearing in an accommodation element and may optionally be angled relative to the tube shaft.

7. The surgical set of instruments according to claim 6, wherein a link joint is present for angling between the tube shaft and the accommodation element.

8. The surgical set of instruments according to claim 7, wherein the tissue applicator has a holder consisting of hooks arranged pivotably in the tube shaft.

9. The surgical set of instruments according to claim 8, wherein the tissue applicator also has a pivotable mandrel for putting up the tissue.

10. A surgical set of instruments, comprising a surgical instrument and a guide device for the treatment of cartilage, bone or body tissue surfaces in the same plane as the areas to be treated, wherein the set comprises a surgical instrument having a bent head and a guide pin on its shank or grip, and the guide device has a circular guide element in the form of a rotatable disk having eccentric, helically arranged bores for optional insertion of a guide pin present on the shank or grip of the surgical instrument, wherein the distance from the respective bore, into which the guide pin is inserted, to the center of the rotatable disk, is referred to as radius c, and said rotatable disk is in the same plane as the area to be treated and is tightly secured to a holder, a guide sleeve for the surgical instrument being affixed to the bottom of the holder via a vertical joint element, the center of said guide sleeve simultaneously representing an invariant point (P), and the size of the area to be treated being determined by selecting the radius c on the rotatable disk and an adjustable distance d between the center of rotatable disk and the center of guide sleeve, where the distance b between the invariant point and the center of the area to be treated is equal to the distance d.

11. The surgical set of instruments according to claim 10, wherein the guide element in the guide device has a graduation.

12. The surgical set of instruments according to claim 11, wherein the set additionally comprises a tissue applicator for applying tissue on a defect to be covered, consisting of a holder for the tissue and a tube shaft, the holder being arranged optionally rotatably and/or pivotably in a bearing in the tube shaft.

13. The surgical set of instruments according to claim 12, wherein the tissue applicator has a forked holder which is rotatably arranged in a bearing in an accommodation element and may optionally be angled relative to the tube shaft.

14. The surgical set of instruments according to claim 13, wherein a link joint is present for angling between the tube shaft and the accommodation element.

15. The surgical set of instruments according to claim 12, wherein the tissue applicator has a holder consisting of hooks arranged pivotably in the tube shaft.

16. The surgical set of instruments according to claim 15, wherein the tissue applicator also has a pivotable mandrel for putting up the tissue.

* * * * *

UNITED STATES PATENT AND TRADEMARK OFFICE
CERTIFICATE OF CORRECTION

PATENT NO.     : 6,663,616 B1
DATED          : December 16, 2003
INVENTOR(S)    : Klaus Roth et al.

It is certified that error appears in the above-identified patent and that said Letters Patent is hereby corrected as shown below:

<u>Title page,</u>
Item [73], Assignee, should be -- Teltow (DE) --

Signed and Sealed this

Sixth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,663,616 B1
DATED        : December 16, 2003
INVENTOR(S)  : Klaus Roth et al.

It is certified that error appears in the above-identified patent and that said Letters Patent is hereby corrected as shown below:

<u>Title page,</u>
Item [75], Inventors, name should be -- Marc Oliver Schurr -- not "Marc Oliver Schurr"

Signed and Sealed this

Seventh Day of September, 2004

JON W. DUDAS
*Director of the United States Patent and Trademark Office*